United States Patent [19]
Antonevich et al.

[11] Patent Number: 5,066,600
[45] Date of Patent: Nov. 19, 1991

[54] MULTIPLE WASTE ISOLATION SYSTEM

[75] Inventors: John M. Antonevich, Jamestown; John E. Sundeen, Lakewood, both of N.Y.

[73] Assignee: Cummins Engine Company, Inc., Columbus, Ind.

[21] Appl. No.: 354,018

[22] Filed: May 19, 1989

[51] Int. Cl.$^5$ .............................................. G01N 35/08
[52] U.S. Cl. ..................................... 436/52; 422/62; 422/81; 137/861; 137/883
[58] Field of Search ...................... 436/53, 52; 422/62, 422/81; 210/424; 137/240, 861, 883; 134/166 R, 169 R; 356/312, 315, 316

[56] References Cited

U.S. PATENT DOCUMENTS 4,645,647 2/1987 Yoshida et al. .................. 422/81
4,722,830 2/1988 Urie et al. ....................... 422/62

Primary Examiner—Robert J. Warden
Assistant Examiner—Laura E. Collins
Attorney, Agent, or Firm—Sixbey, Friedman, Leedom & Ferguson

[57] ABSTRACT

A multiple waste isolation system including a common drain connected to the discharge outlet of an inductively coupled plasma system for atomic spectroscopy. This common drain may be connected to a multiport valve for directing the flow of waste material to a selected one of a plurality of flow paths or the common drain may be connected directly to each flow path with each flow path including individual on/off type valves for selectively allowing flow through the various paths. The system also includes at least two drainage lines either directly connected to the common drain or connected thereto via the multiport valve for isolating a waste product from the other drainage line so as to maintain the separation of potentially incompatible waste products. The system further includes a purging tube which is also connected either directly to the common drain or thereto via the multiport valve for circulating a cleaning solvent through the common drain and the valve. A reservoir is provided for capturing this cleaning solvent which may be either recycled through the system or disposed of. The valve which controls the flow of fluid through the system may be either manually operated or automatically controlled by way of a control computer which controls both the direction of fluid flow through the system as well as the purging of the common drain and the valve.

8 Claims, 4 Drawing Sheets

MULTIPLE WASTE ISOLATION SYSTEM

TECHNICAL FIELD

The present invention relates to a system for draining waste products from a sample testing unit. More particularly, the present invention relates to a system for isolating multiple wastes expended from the testing unit to ensure that potentially incompatible by-products do not interact.

BACKGROUND ART

At the present time, waste disposal from an Inductively Coupled Plasma System for atomic spectroscopy is conducted through a single drain tube assembly connected to a plasma torch unit of the system. As is shown in FIG. 1, this assembly includes a sample introduction system which consists of a neublizer, spray chamber, an outlet to a flame or plasma and a waste outlet. The majority of the sample is discharged from the system as waste through a single drain line. As can be seen from FIG. 2, this drain line consists of flow tubing and a trap T. The trap T is provided to maintain a positive back pressure in the system as well as to provide protection against the build-up of gases within the drain vessel.

Sample preparation for atomic spectroscopy frequently requires the handling of corrosive organic or aqueous solutions. This may require the dilution of liquid samples or the more hazardous procedure of dissolving a solid sample in a solution. These procedures are set forth in Environmental Protection Agency (EPA) guidelines for safe laboratory practice.

During the sampling process, in order to maintain optimum performance of the system, the drain must be kept clean and free flowing. In order to achieve this the drain must be cleaned frequently thereby interrupting the sampling procedure. Further, the drain assembly must be routinely inspected, and any deteriorating portions must be replaced resulting in additional downtime of the sampling system.

It is also often desired to test samples of different types which require various solvents. These various solvents are often incompatible with one another and if mixed could result in a toxic hazardous solution. In order to eliminate any likelihood that those substances will in fact mix, the system is disassembled and cleaned after each use. Again, this procedure is necessary to ensure the safety of the operator, and results in a significant downtime in the operation of the sampling system.

In an effort to minimize the downtime of the analysis system, U.S. Pat. No. 4,722,830 to Urie et al., proposes an automated multiple stream system which provides a plurality of process sample streams whose delivery are controlled by a multiport valve. The system includes a pair of processing systems each being capable of analyzing a variety of samples on command with each having a single waste stream. However, this system is only concerned with the isolation of simultaneous process streams and has not considered the isolation of multiple sequential waste streams.

Clearly, there is a pressing need for a system which is capable of isolating multiple waste streams so as to minimize downtime due to a change in sample selection or maintenance while maintaining a safe environment around the system.

SUMMARY OF THE INVENTION

It is a primary object of the present invention to provide a waste isolation and management system for effectively increasing the analytical capabilities of an inductively coupled plasma sample testing system.

Another object of the present invention is to provide a waste isolation system for effectively isolating multiple waste streams for handling a variety of potentially incompatible waste products.

Yet another object of the present invention is to provide a waste isolation system which effectively handles a variety of potentially incompatible waste products safely so as to not pose any danger to the operator or the environment.

A further object of the present invention is to provide a waste isolation system which minimizes the downtime of the host analytical system due to maintenance of the waste isolation system.

Yet another object of the present invention is to provide a waste management system which may be readily adapted to existing sample testing systems or integrated into future systems.

These, and other objects of the present invention are achieved by providing a multiple waste isolation system including a common drain connected to the discharge outlet of an inductively coupled plasma system for atomic spectroscopy. This common drain may be connected to a multiport valve for directing the flow of waste material to a selected one of a plurality of flow paths or the common drain may be connected directly to each flow path with each flow path including individual on/off type valves for selectively allowing flow through the various paths. The system also includes at least two drainage lines either directly connected to the common drain or connected thereto via the multiport valve for isolating a waste product from the other drainage line so as to maintain the separation of potentially incompatible waste products. The system further includes a purging tube which is also connected either directly to the common drain or thereto via the multiport valve for circulating a cleaning solvent through the common drain and the valve. A reservoir is provided for capturing this cleaning solvent which may be either recycled through the system or disposed of. The valve which controls the flow of fluid through the system may be either manually operated or automatically controlled by way of a control computer which controls both the direction of fluid flow through the system as well as the purging of the common drain and the valve.

The above, as well as additional advantages of the present invention will become apparent from the figures and the following detailed description of the invention.

DETAILED DESCRIPTION OF THE PREFERRED EMBODIMENT

Figure 1:
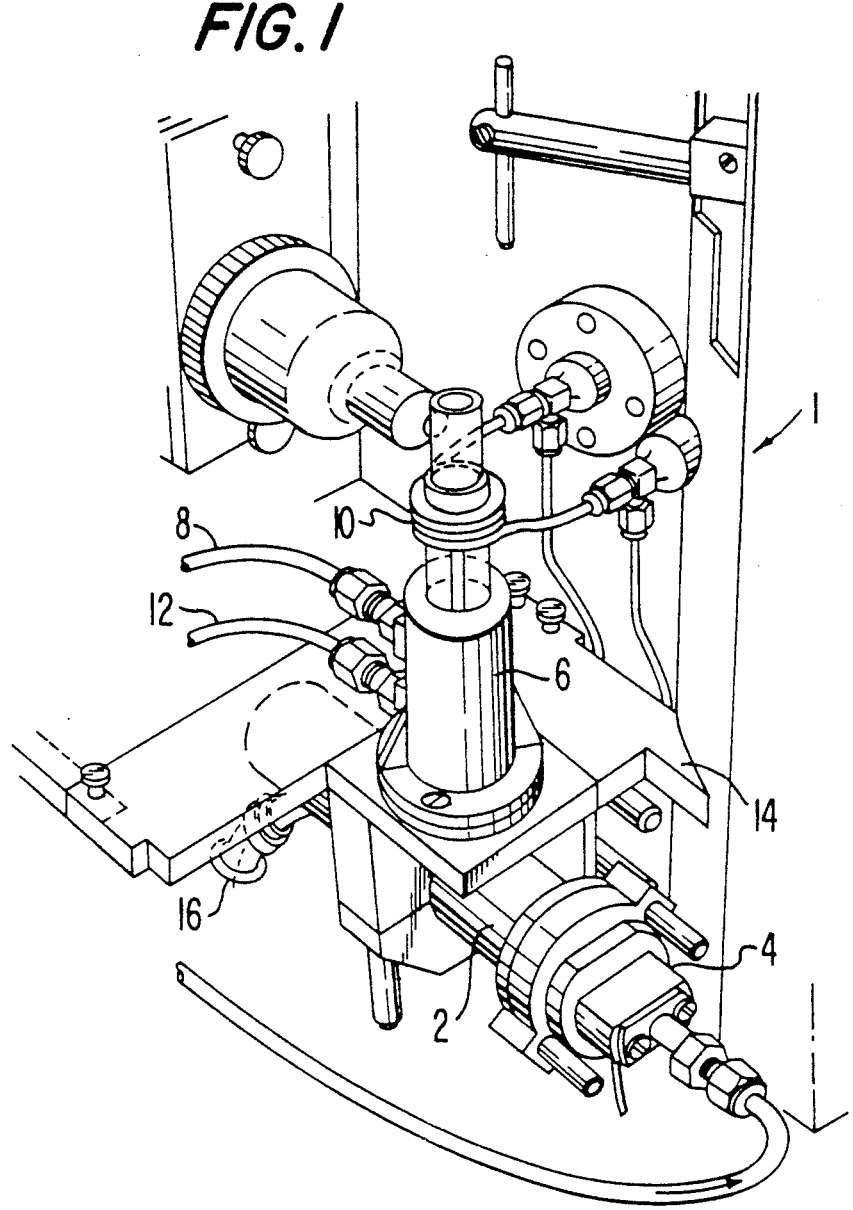
FIG. 1, illustrates the analyzing system to which the waste management system of the present invention is to be attached.

FIG. 1 of the drawings illustrates the inductively coupled plasma analyzing system to which the present invention may be readily adapted or may be integrated in the design of the analyzing system. Analyzing systems of this type have been developed by Perkin-Elmer, Jarrell-Ash as well as others. As is shown in FIG. 1, the analyzing system consist of a spray chamber 2, a neublizer 4, and a torch 6 for generating a plasma to be analyzed. In operation, argon gas is supplied through the torch argon gas inlet 8, and is directed through the torch to inductively generate a plasma by applying radio frequency energy from the four turn coil 10. An auxiliary argon gas supply is provided through the inlet 12 if necessary. The sample to be analyzed may be pumped to the neublizer 4 by a peristaltic pump (not shown) where a sample aerosol is generated by the neublizer which enters the plasma zone where this aerosol spray is subject to extremely high temperatures. The system as well as the operator is protected from these high temperatures by the thermal barrier 14 as well as the housing encompassing the system. It should be noted that the present invention may be readily adapted to other testing devices such as those used for atomic absorption spectroscopy.

Figure 2:
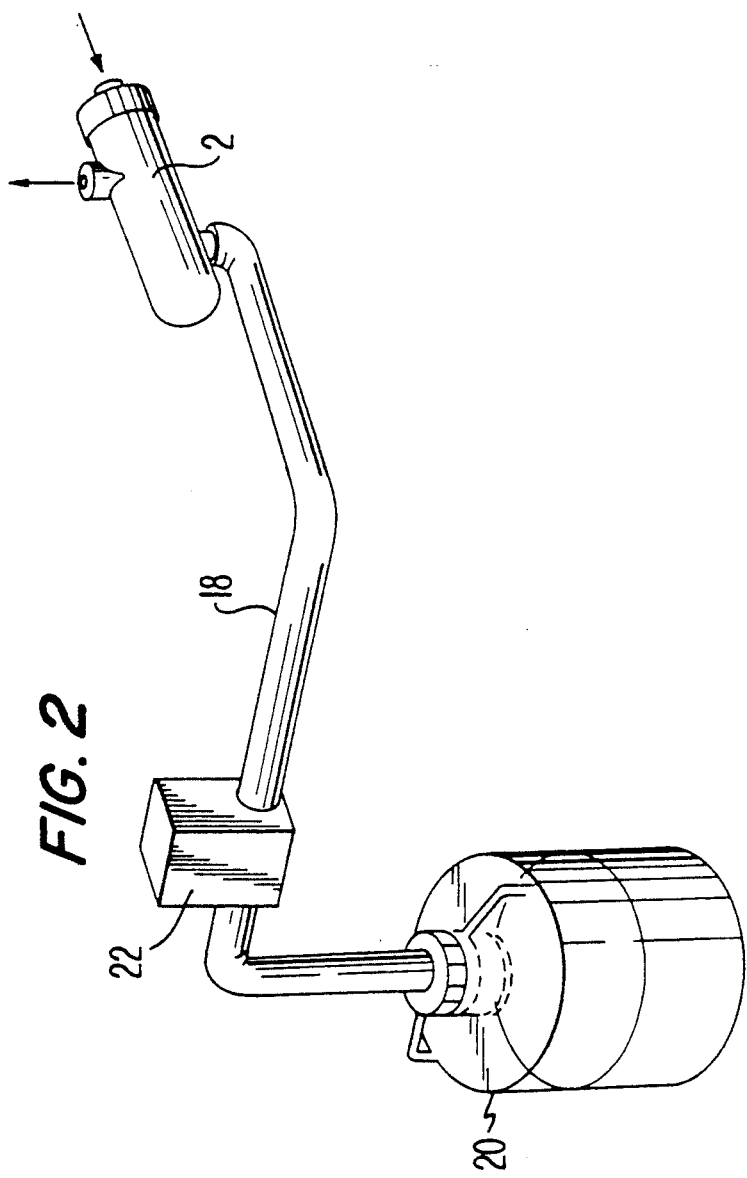
FIG. 2, illustrates a conventional waste disposal system.

During the analysis of a particular sample a majority of the sample is discharged from the spray chamber 2 as waste through the drain 16. Previously, as mentioned above and shown in FIG. 2, this waste material was discharged through a drain tube 18 to a collection vessel 20. A trap 22 is provided in the system for maintaining a sufficient back pressure in the spray chamber so as to result in an accurate sample testing procedure. The subject draining system, however, may require cleaning when the type of sample to be tested is changed and consequently the analyzing system would be rendered inoperable. Further, because the drain tube 18 and much of the trap 22 are formed of a plastic material, some organic liquids may attack and deteriorate the plastic tubing making replacement of the drain necessary. This also adds to the downtime of analyzing system as a whole.

Figure 3:
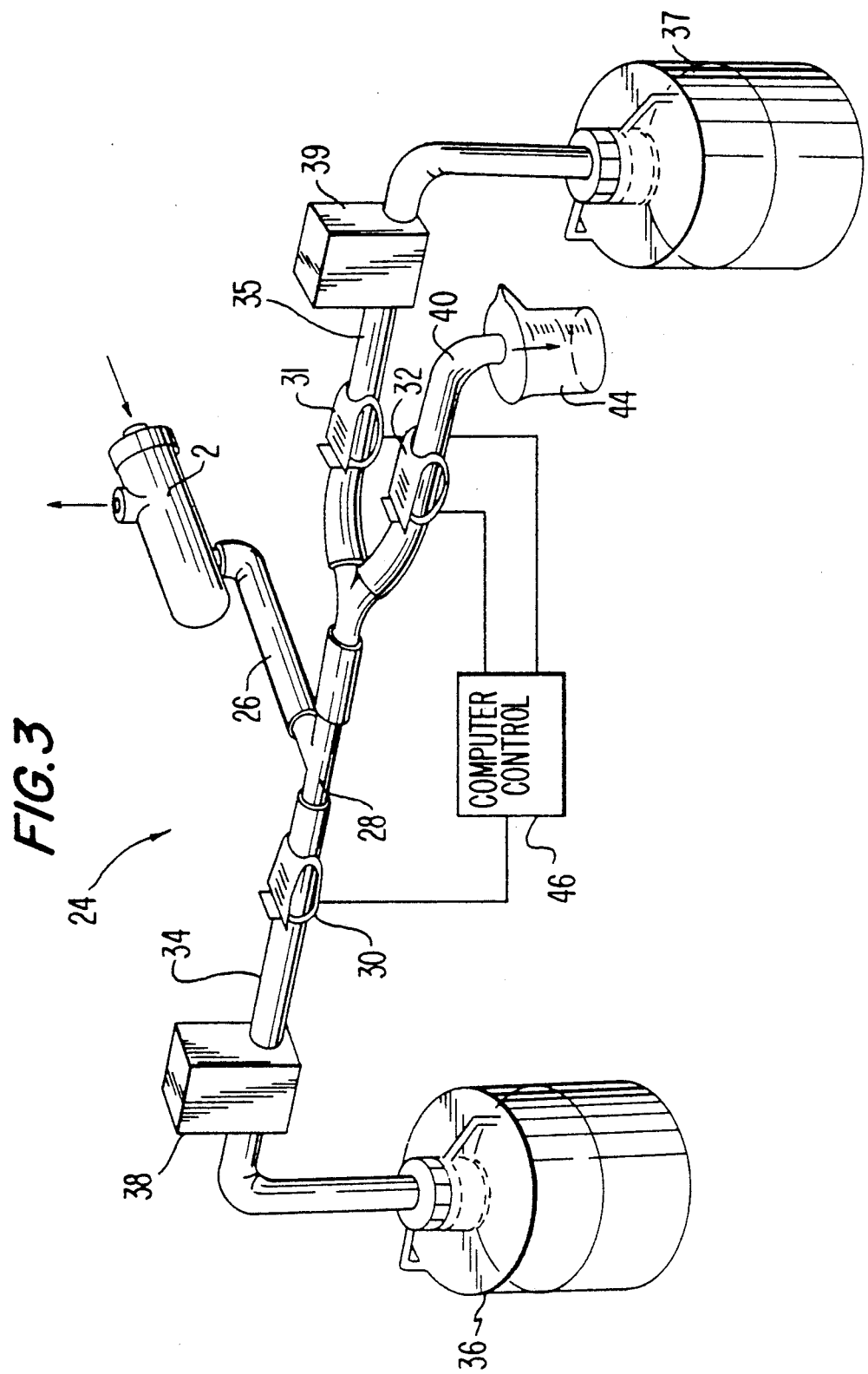
FIG. 3, illustrates an embodiment of the waste isolation and management system in accordance with the present invention.

FIG. 3 illustrates the waste isolation and management system of the present invention which can both safely and efficiently dispose of the excess sample discharged as waste from the spray chamber 2. The waste isolation system 24 includes a common drain 26 which leads to a T 28 for directing the flow of waste product through one of a selected drain line or purge line. The waste isolation system includes three valves 30, 31, and 32 which selectively regulate the flow path of the waste material. During the operation of the analyzing system, one of valves 30, 31, and 32 will be in the open condition while the others will be in the closed position. Valve 30 leads to a drain tube 34 and ultimately to a collection vessel 36. Again, as in the single line drain a trap 38 is positioned within the flow path of the drain assembly in order to maintain a back pressure within the spray chamber 2. Similarly, a drain tube 35 is provided to extend from a second valve 31 for draining waste material to a collection vessel 37. Furthermore, a duplicate trap 39 is provided within the second waste drain tube 35 to perform a function similar to that of trap 38. By providing a dual drainage system, continued operation of the analyzing system can be undertaken even when one of the tube drain lines is inoperable or when it is desired to change testing samples. Also provided within the waste management system 24 is a purge line 40 connected to the valve 32 for purging a common drain 26 and T 28 when it is desired to change testing samples.

Figure 4:
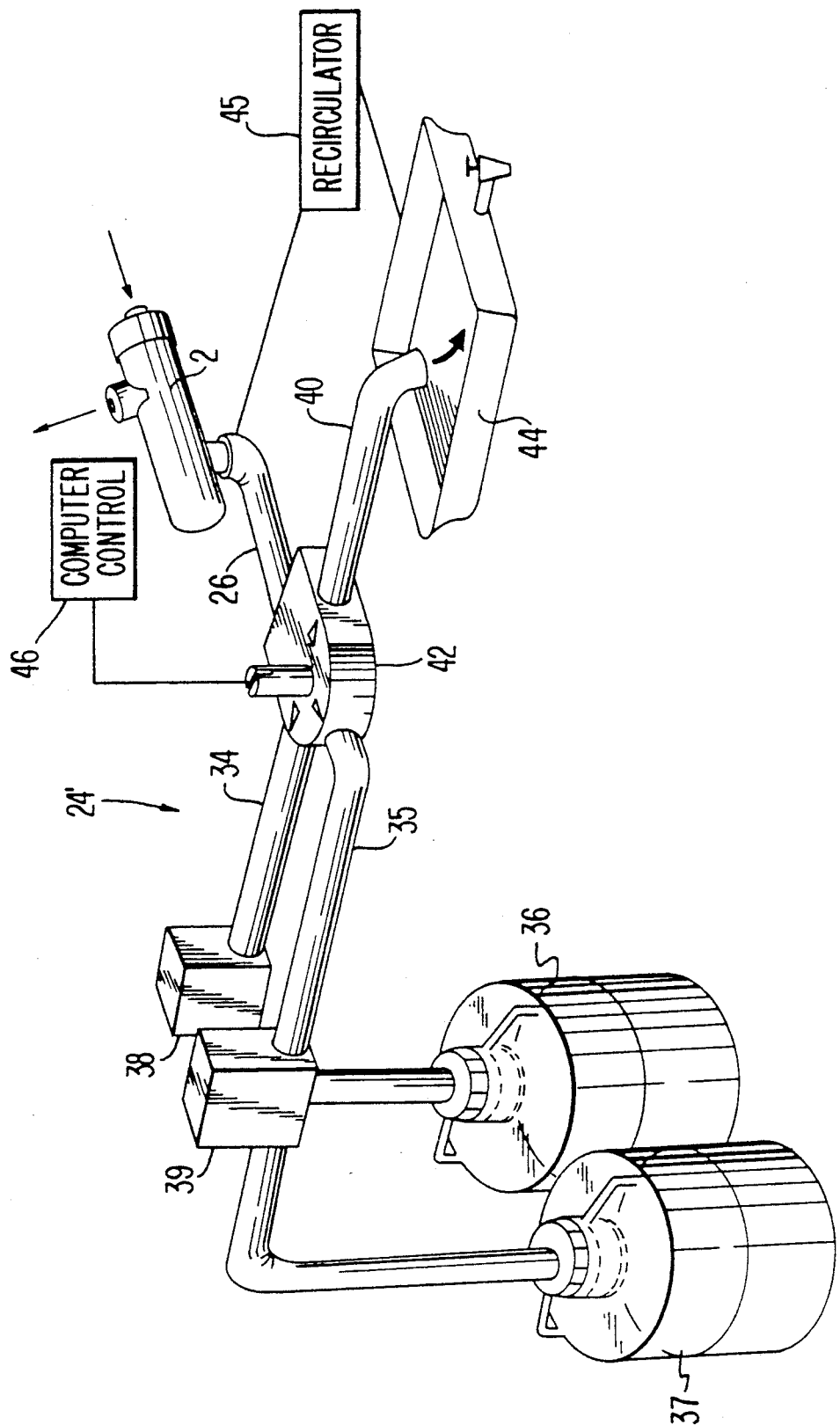
FIG. 4, illustrates a modification of the waste isolation and management system in accordance with the present invention.

FIG. 4 illustrates an alternative embodiment to that illustrated in FIG. 3. Like elements will be referenced to by like numerals in this figure. The waste isolation system 24' of FIG. 4 includes a common drain 26 as well as drain tubes 34 and 35, collection vessels 36 and 37, in line traps 38 and 39, as well as a purging tube 40. Each of the drain tubes 34 and 35 and the purge tube 40 are connected to an outlet of a three way valve 42, with the common drain 26 being connected to a single inlet to the three way valve 42. During operation, the three way valve 42 is set to direct the flow of waste material through one of either drain tube 34 or drain tube 35. This will allow for the competent isolation of a particular waste material. An intermediate positioning of the three way valve 42 will allow the flow of material from the common drain 26 to flow through the purge tube 40. This provision will enhance the cleansing of both the spray chamber and the common drain 26, as well as the valve 42 when desired. It should be noted at this time that if necessary the purge tube may be connected to a temporary third drain line and collection vessel for analyzing yet another possibly incompatible sample material.

Operation of the waste isolations systems of FIGS. 3 and 4 is carried out by initially cleansing the common drain 26 and valves. This may be achieved by closing valves 30 and 31 of FIG. 3 and opening valve 32 to allow a suitable cleaning solvent to be flushed through the common drain 26, T 28, and purge line 40. For the system shown in FIG. 4, the multiport valve 42 is merely rotated to open the outlet port leading to the purge tube 40. During the cleansing of the common drain 26, provisions may be made to agitate the waste isolation system to dislodge any debris which may rest within the lines. Further, the cleansing solution may be permitted to soak within the drain system or may be heated to ensure cleanliness of the common drain 26. The cleansing solution is collected in a beaker or reservoir 44 and may be either disposed of appropriately or recycled through the common drain and valve by a recirculator 45 to further ensure the cleanliness of these components. Once the common drain and valve have been properly cleansed, either valve 32 is closed and one of valves 30 and 31 opened or multi-port valve 42 may be rotated, to selectively open one of lines 34 and 35 depending upon the sample to be analyzed. If the common drain 26 is short in nature and consequently the empty volume of the common drain and valve are small when compared to the volume of fluid in the trap, the mere switching of the valves will complete the transformation of the system from a purge line to the selected drain line. However, if the common drain is long and thereby constitutes a large volume it may be necessary to fill the common drain with the particular sample to be tested in order to provide a free flowing drain as well as to maintain the desire back pressure in the spray chamber 2.

By providing the waste isolation system 24 and 24', drainage and cleaning of the reservoir 44 as well as system inspection, system maintenance and waste handling can be performed while analyzing a given sample thereby minimizing the downtime of this system. It should also be noted that it would be apparent to provide a system having greater than two drainage outputs if it were desired to analyze a greater variety of samples. Consequently, the system may be adapted to isolate the waste expended from any number of samples desired to be tested. It should further be noted at this time that the waste isolation system 24 and 24' may be either manually controlled or automated by way of the computer control 46 depending upon the nature of its use and the desired productivity of the analytical instruments.

While the invention has been described with reference to preferred embodiments, it will be appreciated by those skilled in the art that the invention may be practiced otherwise than as specifically described herein without departing from the spirit and scope of the invention. It is, therefore, to be understood that the spirit and scope of the invention be limited only by the appended claims.

INDUSTRIAL APPLICABILITY

The above described waste isolation system may be employed in any environment where it is desired to maintain the separation of various solutions which may be incompatible and pose dangerous health and safety hazards if combined. The waste isolation system described herein may be employed where incompatible solvents may not be critical but where it is desired to maintain separate waste deposits of given solutions.

We claim:

1. A method of isolating discharged waste from a testing device comprising the steps of:
   a. providing a common drain means connected at a first end to said testing device, a plurality of drainage means connected to a second end of said common drain means for draining fluid passing through said common drain means, a purging means connected to said second end of said common drain means for purging said common drain means and valve means; and
   b. selectively positioning said valve means to direct the flow of fluid through one of said drainage means and said purging means.

2. The method as defined in claim 1, wherein said valve means comprises a plurality of valves, each of said valves being positioned to control the flow of said fluid through a respective one of said drainage means and said purging means, and said step of selectively positioning said valve means includes opening one of said plurality of valves and closing the remaining valves.

3. The method as defined in claim 1, wherein said valve means comprises a single, multiport valve, and said step of selectively positioning said valve means includes rotating said multiport valve to a selected position wherein one of said drainage means and said purging means are operable.

4. The method as defined in claim 1, further including the step of purging said common drain by passing a cleaning solvent through said common drain and said purging means where said valve means is positioned to direct the flow of fluid through said purging means.

5. The method as defined in claim 4, wherein said step of purging includes recirculating said cleaning solvent through said common drain and said purging means.

6. The method as defined in claim 4, further including the step of agitating said common drain, valve means and purging means during the purging of said common drain.

7. The method as defined in claim 4, further including the step of heating said cleaning solvent.

8. The method as defined in claim 1, wherein the positioning of said valve means is carried out automatically by an automation system.

* * * * *